United States Patent [19]

Pawelchak et al.

[11] Patent Number: 4,728,642
[45] Date of Patent: Mar. 1, 1988

[54] METHOD OF TREATING WOUNDS WITH GRANULES AND DRESSING

[75] Inventors: John M. Pawelchak, East Windsor; Frank M. Freeman, Lawrenceville, both of N.J.

[73] Assignee: E. R. Squibb & Sons, Inc., Princeton, N.J.

[21] Appl. No.: 728,421

[22] Filed: Apr. 29, 1985

Related U.S. Application Data

[60] Division of Ser. No. 705,859, Feb. 27, 1985, Pat. No. 4,538,603, which is a continuation of Ser. No. 370,893, Apr. 22, 1982, abandoned.

[51] Int. Cl.$^4$ ............................................. A61K 31/70
[52] U.S. Cl. ........................................ 514/57; 514/54; 514/59; 514/60; 514/2
[58] Field of Search ................. 514/54, 57, 59, 60, 514/2

[56] References Cited

U.S. PATENT DOCUMENTS 3,972,328  8/1976  Chen .................................. 128/156
4,538,603  9/1985  Pawelchak et al. ................ 128/156

Primary Examiner—J. R. Brown
Assistant Examiner—Elli Peselev
Attorney, Agent, or Firm—Lawrence S. Levinson; Stephen B. Davis

[57] ABSTRACT

This invention is directed to an occlusive dressing useful for treating skin lesions and a granular material capable of interacting with wound exudate. Wounds emitting a large amount of fluid can be treated by first packing with the granular material and then covering the wound with the occlusive dressing.

11 Claims, 7 Drawing Figures

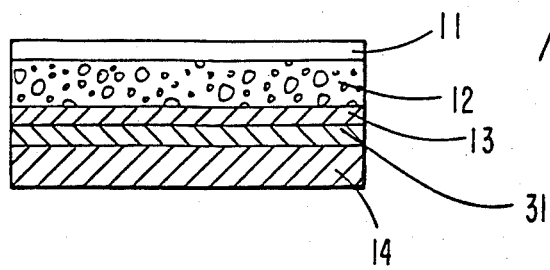
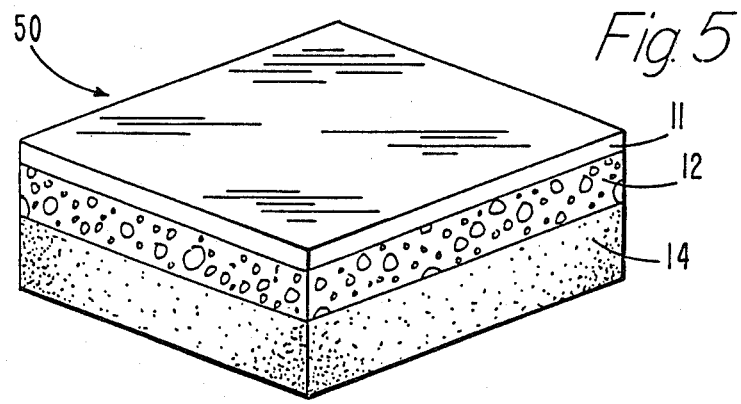
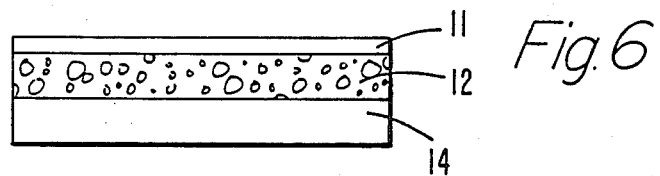
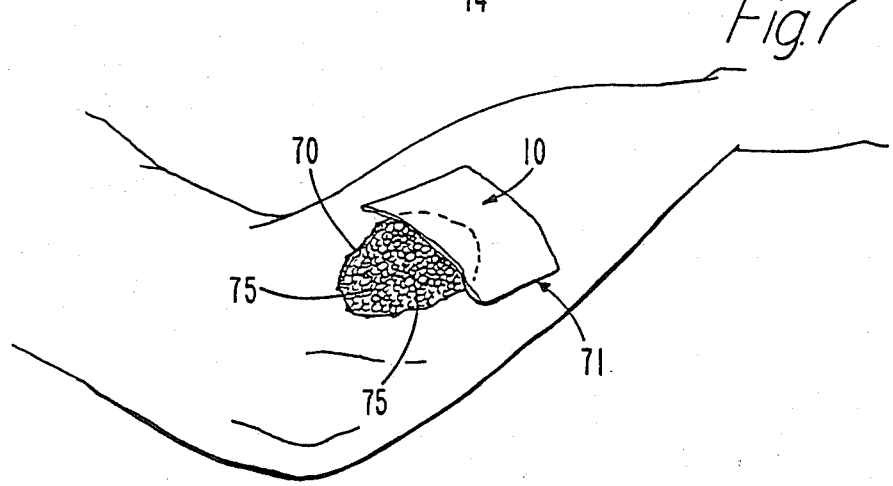

METHOD OF TREATING WOUNDS WITH GRANULES AND DRESSING

This application is a division of U.S. Ser. No. 705,859 filed Feb. 27, 1985, now U.S. Pat. No. 4,538,603, which is a continuation of U.S. Ser. No. 370,893 filed on Apr. 22, 1982, now abandoned.

BACKGROUND OF THE INVENTION

Chen in U.S. Pat. No. 3,972,328 discloses a multi-layer surgical dressing comprising an adhesive layer, a layer of flexible semi-open cell polymeric foam, and an outer water impervious flexible polymeric film coating.

Steer et al. in published United Kingdom Patent Application No. 2,061,732 disclose a multi-layered dressing including a layer of curative and absorbent material (B) which contacts the wound, a layer of deodorizing material (D), and an outer flexible layer (E) that secures the bandage to the body. Layer (B) can be a homogeneous blend (11) of one or more water soluble or swellable hydrocolloids dispersed in a viscous binder and affixed to a semi-open cell polymeric foam (13). A critical feature of this dressing is that layer B has a plurality of apertures (20) extending therethrough.

Chen in U.S. Pat. No. 3,339,546 discloses an adhesive composition comprising a blend of one or more water soluble or water swellable hydrocolloids and a viscous substance such as polyisobutylene. The adhesive mass has a film of water insoluble material affixed to one surface.

Chen et al. in U.S. Pat. No. 4,192,785 describe an adhesive composition suitable for use with an ostomy appliance consisting of a mixture of one or more hydrocolloid gums, a pressure sensitive adhesive such as one or more polyisobutylenes, and a cohesive strengthening agent. The cohesive strengthening agent can be a natural or synthetic fibrous material, finely divided cellulose, cross linked dextran, cross-linked carboxymethyl-cellulose, or a starch-acrylonitrile graft copolymer.

Steinhardt in U.S. Pat. No. 3,029,187 discloses an anhydrous powder blend of gelatin, pectin, and carboxymethylcellulose useful as an adhesive and in pharmaceutical preparations.

Rothman et al. in U.S. Pat. No. 4,225,580 discloses cleansing fluid discharging skin surfaces by the use of a material comprising spherical particles of certain water-insoluble hydrophilic polymers.

SUMMARY OF THE INVENTION

This invention is directed to an occlusive dressing useful for treating skin lesions such as dermal ulcers and pressure sores. This invention is also directed to a method of treating skin wounds which are emitting a large amount of fluid by packing the wound site with a unique granular material and then covering the wound with the occlusive dressing. As treatment progresses and the amount of liquid discharge lessens, the granular packing can be omitted.

This invention is also directed to the composition of the granular packing material.

BRIEF DESCRIPTION OF THE DRAWINGS

FIG. 4 is a front view along line 3—3 of FIG. 3.

FIG. 5 is an overall view of another embodiment of the composite dressing of this invention (greatly enlarged).

FIG. 6 is a front view along line 5—5 of FIG. 5.

FIG. 7 is a top view of an open wound covered by the dressing and partially cutaway to show the granular packing.

DETAILED DESCRIPTION OF THE INVENTION

The Dressing

Figure 1:
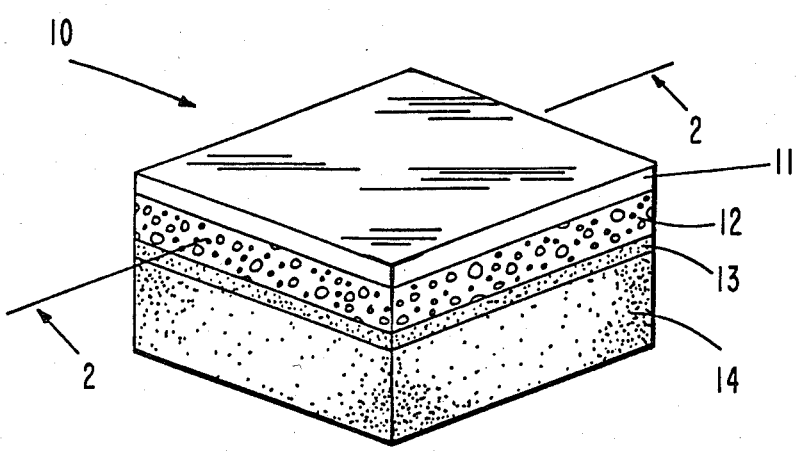
FIG. 1 is an overall view of one embodiment of the composite dressing of this invention (greatly enlarged).
Figure 2:
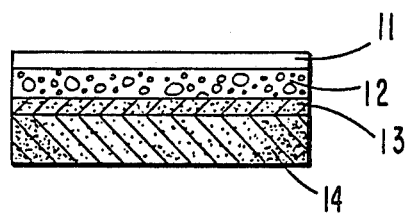
FIG. 2 is a front view along line 2—2 of FIG. 1.

One embodiment of the occlusive dressing 10 of this invention as shown in FIGS. 1 and 2 comprises a first adhesive layer 14 which is formulated from materials selected to interact with fluid discharged from the wound as well as forming a fluid-tight bond with the healthy skin around the wound so as to seal the dressing to the skin. The dressing of this embodiment includes a second adhesive layer 13 formulated of materials which can be cast onto foam layer 12 and will form an aggressive bond when pressed into contact with adhesive layer 14. The layer 12 is a semi-open cell elastic or flexible foam. The outer layer 11 can be a polymeric film or a skin formed on the top of foam layer 12 which serves to protect the exposed surface of the dressing from contamination by water or soil.

Figure 3:
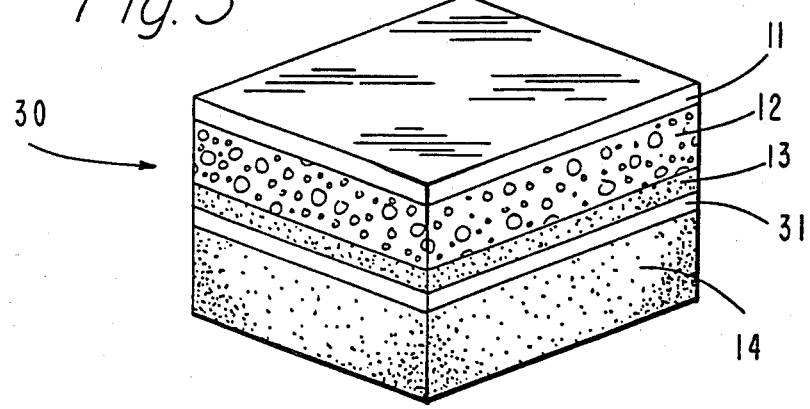
FIG. 3 is an overall view of another embodiment of the composite dressing of this invention (greatly enlarged).

An alternate embodiment of the occlusive dressing is shown as 30 in FIGS. 3 and 4. Dressing 30 includes a layer of deodorizing material designated 31 interposed between adhesive layers 14 and 13.

Another alternate embodiment of the occlusive dressing is shown as 50 in FIGS. 5 and 6. Dressing 50 omits second adhesive layer 13 and has adhesive layer 14 laminated directly to the semi-open cell elastic foam 12.

Adhesive layer 14 comprises a homogeneous blend of one or more pressure sensitive adhesive materials and one or more water dispersible hydrocolloidal materials. Adhesive layer 13 comprises a homogeneous blend of one or more pressure sensitive adhesive materials, one or more water dispersible hydrocolloidal materials, a tackifier, and a plasticizer or solvent. Additionally, one or more thermoplastic elastomers may be included with the pressure sensitive adhesive materials in either or both of layers 14 and 13 and one or more water swellable cohesive strengthening agents and/or one or more natural or synthetic polymers capable of developing elastomeric properties when hydrated may be included with the hydrocolloidal materials in either or both of layers 14 and 13.

Suitable pressure sensitive adhesive materials for inclusion in layers 14 and 13 are various natural or synthetic viscous or elastomeric substances such as natural rubber, silicone rubber, acrylonitrile rubber, polyurethane rubber, polyisobutylene, etc. Low molecular weight polyisobutylenes having a viscosity average molecular weight of from about 36,000 to about 58,000 (Florey) possessing pressure sensitive adhesive properties are preferred. Such polyisobutylenes are commercially available under the trademark Vistanex from Exxon as grades LM-MS and LM-MH.

Optionally, one or more thermoplastic elastomers can be included in the pressure sensitive adhesive component of layers 14 and 13. These elastomers impart the properties of rubber-like extensibility and both rapid and complete recovery from modular strains to the pressure sensitive adhesive component. Suitable thermoplastic elastomers include medium molecular weight polyisobutylenes having a viscosity average molecular weight of from about 1,150,000 to 1,600,000 (Florey), butyl rubber which is a copolymer of isobutylene with a minor amount of isoprene having a viscosity average molecular weight of from about 300,000 to about 450,000 (Florey), and styrene copolymers such as styrene-butadiene-styrene (S-B-S), styrene-isoprene-styrene (S-I-S), and styrene-ethylene/butylene-styrene (S-EB-S) which are commercially available, for example, from Shell Chemical Co. under the trademark Kraton as Kraton D1100, D1102, Kraton D1107, Kraton 4000, Kraton G1600, and Kraton G4600. Preferred thermoplastic elastomers are butyl rubber having a viscosity average molecular weight of about 425,000 (commercially available from Exxon as grade 077), polyisobutylene having a viscosity average molecular weight of about 1,200,000 (commercially available under the trademark Vistanex from Exxon as grade L-100), and styrene-isoprene-styrene (S-I-S)copolymers (commercially available from Shell as Kraton D1107).

The pressure sensitive adhesive component including the optional thermoplastic elastomer is present in adhesive layers 14 and 13 at from about 30% to about 70% by weight of the composition, preferably from about 35% to about 50% by weight. The thermoplastic elastomer can be employed at up to three times the weight of the pressure sensitive elastomeric substances but preferably the theromoplastic elastomer if present will be at from about 20% to about 150% by weight of the pressure sensitive elastomeric substance.

Adhesive layers 14 and 13 include from about 10% to about 65% by weight of one or more water dispersible hydrocolloid materials. Suitable hydrocolloid materials include sodium or calcium carboxymethylcellulose, pectin, gelatin, guar gum, locust bean gum, collagen and gum karaya. Adhesive layers 14 and 13 may also include up to about 50% by weight of one or more water swellable cohesive strengthening agents and/or one or more natural or synthetic polymers capable of developing elastomeric properties when hydrated provided that the water soluble hydrocolloid gums, water swellable cohesive strengthening agents, and hydratable polymers together are present at no more than about 70% by weight of adhesive layers 14 and 13. Suitable water swellable cohesive strengthening agents include finely divided substantially water insoluble cross-linked sodium carboxymethylcellulose such as that commercially available under the trademark Aqualon or that described in U.S. Pat. No. 3,589,364 and available commercially from the Buckeye Cellulose Corp., finely divided substantially water insoluble starch-acrylonitrile graft copolymer such as that described in U.S. Pat. No. 3,661,815 and commercially available from the Grain Processing Corp., and finely divided substantially water insoluble cross-linked dextran such as that commercially available under the trademark Sephadex. Suitably hydratable polymers are gluten and long chain polymers of methyl vinyl ether/maleic acid, preferably, the long chain polymers of methyl vinyl ether/maleic acid commercially available under the trademark Gantrez from GAF Inc. The maleic acid moiety in the polymer may be intact (Gantrez S-97), may be an anhydride (Gantrez AN-169), or may be a metal salt such as the mixed sodium/calcium salts (Gantrez AT-955).

Preferably, the water dispersable hydrocolloids, the optional water swellable cohesive strengthening agents, and the optional hydratable polymers are present at from about 45% to about 65% by weight of adhesive layer 14 and from about 30% to about 50% by weight of adhesive layer 13.

The water dispersable hydrocolloids provide wet tack for adhesive layers 14 and 13 while the pressure sensitive adhesive component provides dry adhesion and imparts structural integrity to layers 14 and 13.

Adhesive layer 13 also includes from about 5% to about 15% by weight of a plasticizer or solvent such as mineral oil or petrolatum with mineral oil being preferred and from about 15% to about 25% by weight of a tackifier such as a terpene resin.

Small amounts, i.e., less than 5% by weight, of other ingredients may be included within adhesive layers 14 and 13. For example, an antioxidant such as butylated hydroxyanisole or butylated hydroxytoluene, a deodorant such as chlorophyllins, or a perfume agent may be included. In addition, small amounts of a pharmacologically active ingredient can be included in adhesive layer 14. For example, an antibiotic or antimicrobial agent such as neomycin, an antiseptic agent such as povidone iodine, and an antiinflammatory agent such as hydrocortisone or triamcinolone acetonide.

The semi-open cell elastic or flexible foam layer 12 can be formed from various elastomer materials such as polyester or polyether polyurethane foams, styrene-butadiene foams, certain rubber based foam, etc. The material should, of course, be non-toxic and stable. The preferred material is a flexible polyurethane foam having from about 50 to about 100 cells per linear inch with about 80 cells per linear inch being most preferred. By semi-open it is meant that the percentage of open or ruptured cells is from about 30 to about 85%.

The outer layer 11 can be a polymeric elastic or flexible film coating formed from a water impermeable pliable elastomer material such as flexible polyurethane, polyacrylate, polyethylene, etc. Layer 11 can be a skin of such polymeric material flame laminated to the top of foam layer 12 by means of heat and/or pressure. The exposed sides of polymeric foam layer 12 can also be coated or heat and/or pressure treated to form an impermeable film or skin. Polyurethane is the preferred material for film or skin 11.

In a typical dressing, adhesive layer 14 will vary in thickness from about 0.02 to about 0.1 inches, preferably about 0.05 inches, adhesive layer 13 will vary in thickness from about 0.005 to about 0.02 inches, preferably about 0.015 inches, foam layer 12 will vary in thickness from about 0.03 to about 0.1 inches, preferably about 0.065 inches and outer layer or skin 11 will vary in thickness from about 0.001 to about 0.003 inches, preferably about 0.002 inches.

As shown in FIGS. 3 and 4, a layer of deodorizing material can be included between the two adhesive layers. Suitable deodorizing materials include a sheet of foamed polymeric material such as polyurethane having a large number of activated carbon particles bound to the matrix of the foam. Such a material is commercially available under the tradename Bondina. Another type of deodorizing material is a paper or felt like substance containing activated carbon such as that commercially available under the tradename K-felt (Toyobo) or Getter paper (Mead). The layer of deodorizing material will vary from about 0.010 to 0.100 inches.

The dressing 10 is prepared as follows. First, adhesive layer 14 is prepared by forming a homogeneous dispersion of the pressure sensitive adhesive material and any thermoplastic elastomer with a heavy duty mixer, e.g., a kneader mixer or sigma blade mixer. The hydrocolloid gums, water swellable cohesive strengthening agents, hydratable polymers, and any other optional ingredients are added and mixing is continued until a homogeneous dough is formed. Alternatively, if layer 14 includes a thermoplastic elastomer, then the elastomer can first be broken down by mixing for several minutes, a portion of the pressure sensitive adhesive material and other ingredients added and mixing continued until a homogeneous mass is formed. The balance of pressure sensitive adhesive is then added and the mixing continued until a homogeneous dough is formed. This dough is then extruded into a thick slab which is thinned down by pressure rollers to the desired thickness.

Next, adhesive layer 13 is prepared by forming a mixture of the hydrocolloid gums, pressure sensitive adhesive materials, tackifier and plasticizer, as well as other optional ingredients such as thermoplastic elastomers, water swellable cohesive strengthening agents, hydratable polymers, antioxidants, etc., in an organic solvent such as heptane or hexane. The resulting adhesive slurry is then applied to a web of silicone coated release paper and the solvent is evaporated. Upon drying the hydrocolloids are dispersed throughout the adhesive layer. This adhesive material is then compressed with a laminate of semi-open cell flexible polymeric foam having a water impermeable polymeric coating or skin on one side.

Finally, the silicone coated release paper is stripped away from adhesive layer 13 and adhesive layers 13 and 14 are pressed together with heat to form the dressing. Silicone coated release paper can then be applied to the exposed surface of adhesive layer 14 and the dressing can be cut to the desired shape and packaged. After packaging, the dressing can be sterilized by gamma irradiation.

Dressing 30 is prepared in a similar manner except that a layer of deodorizing material is laminated between adhesive layers 14 and 13. Alternatively, dressing 30 can be prepared by first laminating adhesive layer 13 directly to the layer of deodorizing material 31 and then attaching this adhesive coated material to foam layer 12. In the case of dressing 50, adhesive layer 14 is prepared as described above and is then laminated while warm directly to foam layer 12 by means of pressure.

The following are representative examples of dressings within the scope of the invention.

EXAMPLE 1

A dressing was prepared having the following composition

Layers 11 and 12

Semi-open cell polyurethane foam having a polyurethane skin flame laminated to one surface.

| | Percent by weight |
|---|---|
| Layer 13 | |
| Polyisobutylene (Vistanex LM-MH) | 18.0 |
| Polyisobutylene (Vistanex L-100) | 20.0 |
| Terpene resin (Piccolyte) | 20.0 |

-continued

| | Percent by weight |
|---|---|
| Butylated hydroxytoluene | 0.5 |
| Mineral oil | 8.5 |
| Sodium carboxymethylcellulose | 18.0 |
| Gelatin | 15.0 |
| Layer 14 | |
| Polyisobutylene (Vistanex LM-MH) | 40 |
| Gelatin | 20 |
| Pectin | 20 |
| Sodium carboxymethylcellulose | 20 |

Adhesive layer 14 was prepared as follows. A premix was prepared by blending 1.4 kg. of gelatin, 1.4 kg. of pectin, and 1.4 kg. of sodium carboxymethylcellulose. The blended premix was added to a heavy duty sigma blade-type mixer followed by the addition of 1.4 kg. of polyisobutylene. After mixing for 10 minutes, an additional 1.4 kg. of polyisobutylene was added and mixing continued until a homogeneous dough was formed (about 10 to 20 minutes). This dough mass while hot and soft was extruded and thinned down by pressure rollers to a thickness of about 0.05 inches.

A laminate of adhesive layer 13 to semi-open cell polymeric foam (layers 12 and 11) was prepared as follows.

A mixture of 0.31 kg. of polyisobutylene (Vistanex L-100), 0.28 kg. of sodium carboxymethylcellulose, and 0.23 kg of gelatin was kneaded. This mixture was added to a solution of heptane containing 0.28 kg. of polyisobutylene (Vistanex LM-MH), 0.31 kg. of piccolyte resin, 8 g. of butylated hydroxytoluene, and 0.13 kg. of mineral oil to form an adhesive slurry. A portion of this slurry was poured onto a sheet of silicone coated release paper and the solvent evaporated to leave an adhesive layer of about 0.015 inches in thickness. This adhesive layer was laminated to a semi-open cell polyurethane foam of 0.065 inches thickness having a polyurethane skin of about 0.002 inches thickness on one surface by gently compressing the adhesive layer to the foam by passing through pressure rollers.

The silicone coated release paper was then stripped from adhesive layer 13 and adhesive layer 13 and adhesive layer 14 were compressed together by passing through pressure rollers. Silicone coated release paper was then pressed onto the exposed surface of adhesive layer 14. The resulting dressing was cut into the desired shape and packaged.

EXAMPLES 2-15

Following the procedure of Example 1 but employing the following ingredients on a weight percent basis in adhesive layer 14 other dressings within the scope of this invention are obtained.

| | Example | | | |
|---|---|---|---|---|
| Ingredient | 2 | 3 | 4 | 5 |
| Polyisobutylene (Vistanex LM-MH) | 40 | 40 | 40 | 40 |
| Guar gum | 25 | 60 | — | 25 |
| Locust bean gum | — | — | — | — |
| Pectin | — | — | — | — |
| Karaya | — | — | — | — |
| Gelatin | — | — | — | — |
| Sodium carboxymethylcellulose | 10 | — | 17.2 | 10 |
| Collagen | — | — | — | — |
| Cross-linked sodium carboxymethyl-cellulose (Aqualon R) | 15 | — | 25.6 | 15 |
| Starch-acrylonitrile graft | — | — | — | — |

-continued

| Ingredient | Example 2 | 3 | 4 | 5 |
|---|---|---|---|---|
| copolymer (Grain Processing Corp. Polymer 35-A-100) | | | | |
| Cross-linked dextran (Sephadex CM-C50) | — | — | — | — |
| Poly(methyl vinyl ether/ maleic acid), mixed calcium, sodium salt (Gantrez AT-955) | 10 | — | 17.2 | 10 |
| Polyisobutylene (Vistanex L-100) | — | — | — | — |
| Butyl rubber (grade 077) | — | — | — | — |
| Styrene-isoprene copolymer (Kraton 1107) | — | — | — | — |

| Ingredient | Example 6 | 7 | 8 | 9 | 10 |
|---|---|---|---|---|---|
| Polyisobutylene (Vistanex LM-MH) | 40 | 40 | 45 | 50 | 20 |
| Guar gum | 30 | 30 | 25 | — | 20 |
| Locust bean gum | — | — | — | 20 | — |
| Pectin | — | — | 15 | — | — |
| Karaya | — | — | — | 20 | — |
| Gelatin | — | — | — | — | — |
| Sodium carboxymethylcellulose | 12 | — | — | — | 10 |
| Collagen | — | 10 | — | — | 10 |
| Cross-linked sodium carboxymethyl-cellulose (Aqualon R) | 18 | — | — | — | 15 |
| Starch-acrylonitrile graft copolymer (Grain Processing Corp. Polymer 35-A-100) | — | — | 15 | — | — |
| Cross-linked dextran (Sephadex CM-C50) | — | — | — | 10 | — |
| Poly(methyl vinyl ether/ maleic acid), mixed calcium, sodium salt (Gantrez AT-955) | — | 20 | — | — | — |
| Polyisobutylene (Vistanex L-100) | — | — | — | — | 25 |
| Butyl rubber (grade 077) | — | — | — | — | — |
| Styrene-isoprene copolymer (Kraton 1107) | — | — | — | — | — |

| Ingredient | Example 11 | 12 | 13 | 14 | 15 |
|---|---|---|---|---|---|
| Polyisobutylene (Vistanex LM-MH) | 30 | 20 | 40 | 40 | 40 |
| Guar gum | — | 20 | — | 20 | — |
| Locust bean gum | — | — | — | — | 20 |
| Pectin | 15 | — | 15 | — | 20 |
| Karaya | — | — | — | — | — |
| Gelatin | 15 | — | 15 | — | — |
| Sodium carboxymethylcellulose | 15 | 20 | 15 | 15 | 10 |
| Collagen | — | — | 15 | 15 | — |
| Cross-linked sodium carboxymethyl-cellulose (Aqualon R) | 10 | — | — | 10 | — |
| Starch-acrylonitrile graft copolymer (Grain Processing Corp. Polymer 35-A-100) | — | — | — | — | 10 |
| Cross-linked dextran (Sephadex CM-C50) | — | 20 | — | — | — |
| Poly(methyl vinyl ether/ maleic acid), mixed calcium, sodium salt (Gantrez AT-955) | — | — | — | — | — |
| Polyisobutylene (Vistanex L-100) | — | — | — | — | — |
| Butyl rubber (grade 077) | 15 | — | — | — | — |
| Styrene-isoprene copolymer (Kraton 1107) | — | 20 | — | — | — |

EXAMPLES 16–23

Following the procedure of Example 1 but employing the ingredients listed below on a weight percent basis in adhesive layer 13 other dressings within the scope of this invention are obtained.

| Ingredient | Example 16 | 17 | 18 | 19 |
|---|---|---|---|---|
| Polyisobutylene (Vistanex LM-MH) | 15 | 15 | 15 | 15 |
| Guar gum | 20 | 15 | — | — |
| Locust bean gum | — | — | 17 | — |
| Pectin | — | — | — | 10 |
| Karaya | — | — | — | — |
| Gelatin | — | — | — | 10 |
| Sodium carboxymethylcellulose | 15 | 15 | 10 | 10 |
| Collagen | — | — | — | — |
| Cross-linked sodium carboxymethyl-cellulose (Aqualon R) | — | 15 | — | — |
| Starch-acrylonitrile graft copolymer (Grain Processing Corp. Polymer 35-A-100) | — | — | — | — |
| Cross-linked dextran (Sephadex CM-C50) | — | — | — | 10 |
| Poly(methyl vinyl ether/ maleic acid), mixed calcium, sodium salt (Gantrez AT-955) | — | — | 10 | — |
| Polyisobutylene (Vistanex L-100) | — | — | 20 | 15 |
| Butyl rubber (grade 077) | 20 | — | — | — |
| Styrene-isoprene copolymer (Kraton 1107) | — | 19.5 | — | — |
| Mineral oil | 9.5 | 5 | 7.5 | 9.5 |
| Piccolyte resin | 20 | 15 | 20 | 20 |
| Butylated hydroxytoluene | 0.5 | 0.5 | 0.5 | 0.5 |

| Ingredient | Example 20 | 21 | 22 | 23 |
|---|---|---|---|---|
| Polyisobutylene (Vistanex LM-MH) | 15 | 15 | 20 | 15 |
| Guar gum | 15 | 15 | 25 | — |
| Locust bean gum | — | — | — | — |
| Pectin | — | — | — | — |
| Karaya | — | — | — | 10 |
| Gelatin | — | — | — | — |
| Sodium carboxymethylcellulose | 10 | — | — | 15 |
| Collagen | — | — | 5 | — |
| Cross-linked sodium carboxymethyl-cellulose (Aqualon R) | — | 10 | — | — |
| Starch-acrylonitrile graft copolymer (Grain Processing Corp. Polymer 35-A-100) | 10 | — | — | — |
| Cross-linked dextran (Sephadex CM-C50) | — | — | — | 10 |
| Poly(methyl vinyl ether/ maleic acid), mixed calcium, sodium salt (Gantrez AT-955) | — | 10 | — | — |
| Polyisobutylene (Vistanex L-100) | 20 | 20 | 15 | 20 |
| Butyl rubber (grade 077) | — | — | — | — |
| Styrene-isoprene copolymer (Kraton 1107) | — | — | — | — |
| Mineral oil | 9.5 | 9.5 | 9.5 | 9.5 |
| Piccolyte resin | 20 | 20 | 25 | 20 |
| Butylated hydroxytoluene | 0.5 | 0.5 | 0.5 | 0.5 |

The Granules

The wound packing material is a granular product of from about 10 to about 40 mesh particle size and comprises a water dispersable hydrocolloidal material or a mixture of such materials. The granular product can also optionally include up to about 50% by weight of one or more water swellable cohesive strengthening agents and/or one or more hydratable polymers. Suitable water dispersible hydrocolloidal materials include sodium and calcium carboxymethylcellulose, pectin, gelatin, guar gum, locust bean gum, collagen, and gum karaya. Suitable water swellable cohesive strengthening agents include finely divided substantially water insoluble cross-linked sodium carboxymethylcellulose such as that commercially available under the trademark Aqualon or that described in U.S. Pat. No. 3,589,364 and available commercially from the Buckeye Cellulose Corp., finely divided substantially water insoluble starch-acylonitrile graft copolymer such as that described in U.S. Pat. No. 3,661,815 and commercially available from the Grain Processing Corp., and finely divided substantially water insoluble cross-linked dextran such as that commercially available under the trademark Sephadex. Suitably hydratable polymers are gluten and long chain polymers of methyl vinyl ether/maleic acid, preferably, the long chain polymers of methyl vinyl ether/maleic acid commercially available under the trademark Gantrez from GAF Inc. The maleic acid moiety in the polymer may be intact (Gantrez S-97), may be an anhydride (Gantrez AM-169), or may be a metal salt such as the mixed sodium/calcium salts (Gantrez AT-955).

Small amounts, i.e., less than 5% by weight, of other ingredients may be included within or sprayed onto the granules. For example, an antioxidant such as butylated hydroxyanisole or butylated hydroxytoluene, a deodorant such as chlorophyllins, or a perfume agent may be included. In addition, small amounts of a pharmacologically active ingredient can be included within or sprayed onto the granules. For example, an antibiotic or antimicrobial agent such as neomycin, an antiseptic agent such as povidone iodine, and an antiinflammatory agent such as hydrocortisone or triamcinolone acetonide.

The granules preferably contain at least 70% by weight of one or more water dispersable hydrocolloids selected from pectin, gelatin, sodium carboxymethylcellulose, and collagen with a granular product consisting of an equal weight percent mixture of pectin, gelatin, and sodium carboxymethylcellulose being most preferred.

The granular material can be prepared from the powder ingredients by dry compaction, wet granulation, or fluidized bed granulation techniques. The dry compaction method involves blending the component powders, compacting into a slab, and milling the slab to the desired particle size. The milled material is sieved and particles of the proper size range are gathered and packaged.

In the wet granulation process, the powders after blending, or simultaneously with blending, are moistened with water, a hydroalcoholic solution, or low concentration dispersion of one or more of the water dispersable hydrocolloids in water or hydroalcoholic vehicles. Normally, the amount of moisture added is up to about 50% of the dry weight of the powders in order to form granules with adequate process-ability and resistance to attrition. After thorough mixing, the moistened mass is forced through a screen or die to yield granules directly or to yield by extrusion, a particulate noodle-like or ribbon-like mass of material. When dried, this material is then milled to the desired sieve size and packaged. Alternatively, the moistened mass may first be broken into large lumps which are then dried and milled to the desired particle size.

In the fluid bed granulation procedure, the moistening fluid is added to a charge of the blended powders held suspended on a column of rising warm air where the powders are allowed to mix with the granulating fluid, which is very rapidly evaporated, leaving behind agglomerated granules. Less moistening fluid is required in this process then in the wet granulation process described above.

EXAMPLE 24

To 120 kg. of a mixture of equal parts of gelatin, pectin and sodium carboxymethylcellulose were added about 50 liters of distilled water or a mixture of water and ethanol. Mixing was performed in a rotating oscillating device to produce a homogeneous blend. The blend was screened through a coarse sieve (0.5 inch) and the moistened material was dried at 55° C. for 24 hours. The dried material was milled and screened to between 16 and 20 mesh.

EXAMPLES 25-35

Following the procedure of Example 24 but employing the ingredients listed below on a weight percent basis other granular products within the scope of this invention are obtained.

| Ingredient | Example 25 | Example 26 | Example 27 | Example 28 |
|---|---|---|---|---|
| Guar gum | — | — | — | — |
| Locust bean gum | — | — | — | — |
| Pectin | 25 | 50 | — | — |
| Karaya | — | — | — | — |
| Gelatin | 25 | — | 50 | — |
| Sodium carboxymethylcellulose | 25 | — | — | 50 |
| Calcium carboxymethylcellulose | — | — | — | — |
| Collagen | 25 | 50 | 50 | 50 |
| Cross-linked sodium carboxymethylcellulose (Aqualon R) | — | — | — | — |
| Starch-acrylonitrile graft copolymer (Grain Processing Corp. Polymer 35-A-100) | — | — | — | — |
| Cross-linked dextran (Sephadex CM-C50) | — | — | — | — |
| Poly(methyl vinyl ether/maleic acid), mixed calcium, sodium salt (Gantrez AT-955) | — | — | — | — |

| Ingredient | Example 29 | Example 30 | Example 31 | Example 32 |
|---|---|---|---|---|
| Guar gum | 20 | — | — | — |
| Locust bean gum | — | — | 20 | — |
| Pectin | 20 | 23.3 | — | 20 |
| Karaya | — | — | 20 | — |
| Gelatin | — | 23.3 | — | 20 |
| Sodium carboxymethylcellulose | 40 | 23.4 | 60 | 20 |
| Calcium carboxymethylcellulose | 20 | — | — | — |
| Collagen | — | — | — | 20 |
| Cross-linked sodium carboxymethylcellulose (Aqualon R) | — | 20 | — | — |
| Starch-acrylonitrile graft copolymer (Grain Processing Corp. Polymer (35-A-100) | — | — | — | 20 |
| Cross-linked dextran (Sephadex CM-C50) | — | — | — | — |
| Poly(methyl vinyl ether/maleic acid), mixed calcium, sodium salt (Gantrez AT-955) | — | 10 | — | — |

| Ingredient | Example 33 | Example 34 | Example 35 |
|---|---|---|---|
| Guar gum | — | — | — |
| Locust bean gum | — | — | — |
| Pectin | 20 | 25 | 20 |
| Karaya | — | — | — |
| Gelatin | 20 | 25 | 20 |
| Sodium carboxymethylcellulose | 20 | 25 | 20 |
| Calcium carboxymethylcellulose | — | — | — |
| Collagen | 10 | — | 20 |
| Cross-linked sodium carboxy- | — | 25 | 20 |

-continued

| Ingredient | Example 33 | 34 | 35 |
|---|---|---|---|
| methylcellulose (Aqualon R) | — | — | — |
| Starch-acrylonitrile graft copolymer (Grain Processing Corp. Polymer 35-A-100) | — | — | — |
| Cross-linked dextran (Sephadex CM-C50) | 20 | — | — |
| Poly(methyl vinyl ether/maleic acid), mixed calcium, sodium salt (Gantrez AT-955) | 10 | — | — |

Method of Treating Skin Wounds

The use of the occlusive dressings described above results in a closed moist wound treatment environment. Unlike gauze type dressings, the ingredients employed in adhesive layer 14 permit the dressings of this invention to remain in place over the wound for up to several days. It is believed that the need to frequently change a dressing disturbs the wound healing environment and results in a slower healing process.

The water dispersible hydrocolloid materials, the water swellable cohesive strengthening agents, and the hydratable polymers distributed throughout adhesive layer 14 react in the presence of moisture. In the area of normal skin surrounding the wound site, the layer 14 will gradually hydrate over a period of days. The initial aggressive bond of the dressing to this normal skin is due to the presence of the pressure sensitive adhesive materials in layer 14; i.e., dry tack. As this bond is lessened by perspiration and leakage of moisture under layer 14, the wet tack of the moisture active ingredients in layer 14 becomes more critical in bonding the dressing to the skin. Eventually, layer 14 becomes so hydrated that the dressing can be removed without stripping or macerating the skin around the wound site.

When the dressing is applied over a fluid emitting wound such as a dermal ulcer, it has been observed that the moisture active ingredients in layer 14 will be converted to an almost gel-like mass. This provides an ideal moist environment for cell migration ensuring easy dressing removal with a minimum of damage to the newly formed tissues.

In treating ulcers emitting a large volume of exudate, it has been found to be useful to first pack the wound with the granular material described above and then cover with the occlusive dressing. The granules interact with the wound exudate to form a gel-like mass and prevent leakage through the dressing. As a result, the dressing is changed less often which is believed to result in a shortened healing period. After removal of the dressing, the hydrated granules can be removed from the wound site by flushing with saline solution. As healing progresses and less exudate is present in the wound site, the dressing can be employed without the granular packing.

FIG. 7 shows an ulcer 70 covered by occlusive dressing 10. The dressing is partially broken away to show the granular packing material 75. Of course, adhesive layer 14 contacts the granules 75 in the area of the wound and also bonds the dressing to the normal skin 71 surrounding the ulcer.

What is claimed is:

1. The method of treating a dermal ulcer emitting a large amount of exuadate comprising packing the ulcer with granules capable of interacting with the exudate and then overlaying the ulcer with an occlusive dressing having an adhesive layer which also is capable of reacting with the exudate and of forming a bond with the normal skin surrounding said ulcer wherein said granules have a particle size of from about 10 to about 40 mesh and consist essentially of one or more water dispersible hydrocolloids selected from the group consisting of sodium carboxymethylcellulose, calcium carboxymethylcellulose, pectin, gelatin, guar gum, locust bean gum, collagen and gum karaya, and from zero to 50% by weight of one or more water swellable cohesive strengthening agents, one or more hydratable polymers, and mixtures thereof wherein said water swellable cohesive strengthening agents if present are selected from the group consisting of water-insoluble cross-linked sodium carboxymethylcellulose, water-insoluble starch-acrylonitrile graft copolymer, and water-insoluble cross-linked dextran and wherein said hydratable polymers if present are selected from the group consisting of gluten and long chain polymers of methyl vinyl ether/maleic acid and wherein said occulusive dressing is a multi-layered dressing consisting essentially of an adhesive layer which in use contacts the wound and the surrounding normal skin, an intermediate layer of semi-open cell polymeric foam bonded to the upper surface of said adhesive layer, and an outer moisture impervious polymeric film coated or laminated to the upper surface of said foam layer, wherein said wound and skin contacting adhesive layer consists of from about 35% to about 50% by weight of low molecular weight polyisobutylenes and from about 45% to about 65% by weight of one or more water dispersible hydrocolloids selected from the group consisting of sodium carboxymethylcellulose, calcium carboxymethylcellulose, pectin, gelatin, guar gum, locust bean gum, collagen, and gum karaya.

2. The method of treating a dermal ulcer emitting a large amount of exudate comprising packing the ulcer with granules capable of interacting with the exudate and then overlaying the ulcer with an occlusive dressing having an adhesive layer which also is capable of reacting with the exudate and of forming a bond with the normal skin surrounding said ulcer wherein said granules have a particles size of from about 10 to about 40 mesh and consists of an equal weight percent mixture of pectin, gelatin, and sodium carboxymethylcellulose and said occlusive dressing is a multi-layered dressing consisting essentially of an adhesive layer which in use contacts the wound and the surrounding normal skin, said adhesive layer being from about 0.02 to about 0.1 inches in thickness, an intermediate layer of semi-open cell polyurethane foam bonded to the upper surface of said adhesive layer, said foam layer being from about 0.03 to about 0.1 inches in thickness, and an outer moisture impervious polyurethane film coated or laminated to the upper surface of said foam layer, said film being from about 0.001 to about 0.003 inches in thickness, wherein said wound and skin contacting adhesive layer is a homogeneous blend of about 40% by weight of low molecular weight polyisobutylene, about 20% by weight of sodium carboxymethylcellulose, about 20% by weight of pectin, and about 20% by weight of gelatin.

3. The method of treating a dermal ulcer emitting a large amount of exudate comprising packing the ulcer with granules capable of interacting with the exudate and then overlaying the ulcer with an occlusive dressing having an adhesive layer which also is capable of reacting with the exudate and of forming a bond with the normal skin surrounding said ulcer wherein said granules have a particle size of from about 10 to about 40 mesh and consist essentially of one or more water dispersible hydrocolloids selected from the group consisting of sodium carboxymethylellulose, calcium carboxymethylcellulose, pectin, gelatin, guar gum, locust bean gum, collagen and gum karaya, and from zero to 50% by weight of one or more water swellable cohesive strengthening agents, one or more hydratable polymers, and mixtures thereof wherein said water swellable cohesive strengthening agents if present are selected from the group consisting of water-insoluble cross-linked sodium carboxymethylcellulose, water-insoluble starch-acrylonitrile graft copolymer, and water-insoluble cross-linked dextran and wherein said hydratable polymers if present are selected from the group consisting of gluten and long chain polymers of methyl vinyl ether/maleic acid and wherein said occlusive dressing is a multi-layered dressing consisting essentially of a first adhesive layer which in use contacts the wound and the surrounding normal skin, a second adhesive layer bonded to the top surface of said first adhesive layer, an intermediate layer of semi-open cell polymeric foam bonded to the upper surface of said second adhesive layer, and an outer moisture impervious polymeric film coated or laminated to the upper surface of said foam layer, wherein said first adhesive layer consists of from about 35% to about 50% by weight of low molecular weight polyisobutylene and from about 45% to about 65% by weight of one or more water dispersible hydrocolloids selected from the group consisting of sodium carboxymethylcellulose, calcium carboxymethylcellulose, pectin, gelatin, guar gum, locust bean gum, collagen, and gum karaya and wherein said second adhesive layers consists of from about 35% to about 50% by weight of low molecular weight polyisobutylenes and one or more optional thermoplastic elastomers selected from the group consisting of medium molecular weight polyisobutylenes, butylenes, butyl rubber, aand styrene-isoprene-stryrene copolymers, from about 30% to about 50% by weight of one or more water dispersible hydrocolloids selected from the group consisting of sodium carboxymethylcellulose, calcium carboxymethylcellulose, pectin, gelatin, guar gum, locust bean gum, collagen, and gum karaya, from about 5% to about 15% by weight of mineral oil, from about 15% to about 25% by weight of a terpene resin tackifier, and less than about 5% by weight of one or more anti-oxidants, deodorants, and perfume agents.

4. The method of treating a dermal ulcer emitting a large amount of exudate comprising packing the ulcer with granules capable of interacting with the exudate and then overlaying the ulcer with an occulusive dressing having an adhesive layer which also is capable of reacting with the exudate and of forming a bond with the normal skin surrounding said ulcer wherein said granules have a particle size of from about 10 to about 40 mesh and consist of an equal weight percent mixture of pectin, gelatin, and sodium carboxymethylcellulose and said occulusive dressing is a multi-layered dressing consisting essentially of a first adhesive layer which in use contacts the wound and the surrounding normal skin, said first adhesive layer being of from about 0.02 to about 0.1 inches in thickness, a second adhesive layer bonded to the top surface of said first adhesive layer, said second adhesive layer being from about 0.005 to about 0.02 inches in thickness, an intermediate layer of semi-open cell polyurethane foam bonded to the upper surface of said second adhesive layer, said foam being from about 0.03 to about 0.1 inches in thickness, and an outer moisture impervious polyurethane film coated or laminatred to the upper surface of said foam layer, said film being from about 0.001 to about 0.003 inches in thickness, wherein said wound and skin contacting first adhesive layer is a homogenous blend of about 40% by weight of low molecular weight polyisobutylene, about 20% by weight of sodium carboxymethylcellulose, about 20% by weight of pectin, and about 20% by weight of gelatin, and wherein said second adhesive layer is a homogeneous blend of from about 18% by weight of low molecular weight polyisbutylenes, about 20% by weight of medium molecular weight polyisobutylenes, about 18% by weight of sodium carboxymethylcellulose, about 15% by weight of gelatin, about 20% by weight of terpene resin, about 8.5% by weight of mineral oil, and about 0.5% by weight of butylated hydroxytoluene.

5. The method of claim 1 wherein said wound and skin contacting adhesive layer is a homogeneous blend of about 40% by weight of low molecular weight polyisobutylene, about 20% by weight of sodium carboxymethylcellulose, about 20% by weight of pectin, and about 20% by weight of gelatin.

6. The method of claim 5 wherein said semi-open cell polymeric foam is polyurethane foam and said water impervious polymeric film is polyurethane.

7. The method of claim 6 wherein said wound and skin contacting adhesive layer is from about 0.02 to about 0.1 inches in thickness, said polyurethane foam layer is about 0.03 to about 0.1 inchs in thickness, and said water impervious polyurethane layer is about 0.001 to about 0.003 inches in thickness.

8. The method of claim 3 wherein said wound and skin contacting adhesive layer is a homogenous blend of about 40% by weight of low molecular weight polyisobutylene, about 20% by weight of sodium carboxymethylcellulose, about 20% by weight of pectin, and about 20% by weight of gelatin.

9. The method of claim 8 wherein said second adhesive layer is a homogeneous blend of from about 18% by weight of low molecular weight polyisobutylenes, about 20% by weight of medium molecular weight polyisobutylenes, about 18% by weight of sodium carboxymethylcellulose, about 15% by weight of gelatin, about 20% by weight of terpene resin, about 8.5% by weight of mineral oil, and about 0.5% by weight of butylated hydroxytoluene.

10. The method of claim 9 wherein said semi-open cell polymeric foam is polyurethane foam and said water impervious polymeric film is polyurethane.

11. The method of claim 10 wherein said wound and skin contacting adhesive layer is from about 0.02 to about 0.1 inches in thickness, said second adhesive layer is from about 0.005 to about 0.02 inches in thickness said polyurethane foam layer is about 0.03 to about 0.1 inches in thickness, and said water impervious polyurethane layer is about 0.001 to about 0.003 inches in thickness.

* * * * *